United States Patent

Simonetta et al.

[11] Patent Number: 4,721,604
[45] Date of Patent: Jan. 26, 1988

[54] THERMAL CRACKING FURNACE FOR PRODUCING VINYL CHLORIDE

[75] Inventors: Marco Simonetta, Milan; Giacomo Di Claudio, San Donato Milanese, both of Italy

[73] Assignee: Snamprogetti S.p.A., Milan, Italy

[21] Appl. No.: 897,107

[22] Filed: Aug. 15, 1986

[30] Foreign Application Priority Data

Sep. 5, 1985 [IT] Italy ................... 22068 A/85

[51] Int. Cl.$^4$ .................. F27B 17/00; F27D 7/00
[52] U.S. Cl. .................... 422/189; 422/198
[58] Field of Search ........... 422/198, 200, 187, 189; 196/110, 134; 122/DIG. 1, DIG. 2; 432/92, 221, 223

[56] References Cited

U.S. PATENT DOCUMENTS 3,580,959  5/1971  Dorner .................... 422/198
4,162,290  7/1979  Crawford et al. ............ 422/198

FOREIGN PATENT DOCUMENTS 1409872 10/1975 United Kingdom ......... 122/DIG. 2

Primary Examiner—Barry S. Richman
Assistant Examiner—Joye L. Woodard
Attorney, Agent, or Firm—Hedman, Gibson, Costigan & Hoare

[57] ABSTRACT

The invention relates to an apparatus for the production of vinyl chloride by starting from dichloroethane, wherein dichloroethane is heated, without being vaporized, in the convective section of an oven, it is then vaporized by indirect heat exchange with air or another fluid, which is heated in its turn by exploiting the heat of the cracking products leaving that oven, and containing monomer vinyl chloride. Dichloroethane, as vapor, is introduced into the radiant section of the oven, wherein it undergoes the cracking and forms vinyl chloride and, if it has been used, a portion of the air heated by the heat of the cracking products can be delivered to the oven burners. The system for carrying out the process is illustrated in FIGS. from 1 to 3, and to them reference is made.

10 Claims, 4 Drawing Figures

THERMAL CRACKING FURNACE FOR PRODUCING VINYL CHLORIDE

FIELD OF THE INVENTION

The present invention relates to a process for the production of monomer vinyl chloride by means of the cracking of dichloroethane, and to a system suitable to carry out the process.

BACKGKROUND OF THE INVENTION

According to the technology of the prior art for the production of monomer vinyl chloride by the cracking of dichloroethane, this latter is pre-heated, vapourized, overheated and cracked inside one single piece of equipment heated by combustion (oven) and heat exchange by irradiation and convection from the combustion products towards the stream of dichloroethane. According to this technology, the enthalpy contained in the reaction products at the outlet of the oven, at the typical temperatures of from 450° to 550° C., is no longer used in the plant; the stream of outflowing products is quickly cooled to decrease the reaction rate of undesired reactions, but the enthalpy is not recovered for purposes useful to the system. Furthermore, according to the technology of the prior art, the stream of dichloroethane is vapourized inside the same oven, while being in contact with the combustion products at very high temperature, causing the production of dichloroethane breakdown products, among which coke and coal, which act as precursors of formation of further coke and coal in the irradiation section, which in its turn is quickly fouled up to render the oven no longer operable if not to prejudice of its integrity; the equipment must be hence shut off and submitted to the decoking operation to clean the inner surface of the tubes, with a frequency of about 3-5 times a year.

A variant of the known technology consists in vapourizing the charge in a heat exchanger external to the oven, by using steam, the consumption of which becomes however a considerable expenditure item among the plant consumptions, by it being always produced at expense of valuable fuels.

It has been surprisingly found that reducing the consumptions of fuel is possible, by using the enthalpy of the efficent from the oven to the purpose of both vapourizing the charge and overheating the combustion air, and that increasing is possible the operating time between two subsequent oven decoking operations, by very quickly cooling the efficent from the oven and vapourizing the charge by a high-temperature source at a temperature lower than of the fumes of the known art.

A first object of the present invention is a process for the production of monomer vinyl chloride by dichloroethane cracking, comprising feeding a stream of dichloroethane to the convective section of an oven, so to heat it up to a temperature lower than its boiling temperature under the pressure used, vapourizing the dichloroethane stream outflowing from the convective section of the oven in an area external to said oven, by indirect heat exchange with a hot gaseous fluid, selected from the oven combustion products, nitrogen and/or air, either alone or as mixtures with one another, heated by indirect heat exchange with the hot dichloroethane breakdown (cracking) products outflowing from said oven, drawing the stream of vapourized dichloroethane from said external area, and introducing it into the radiant section of said oven, the heat in the radiant section being supplied by the combustion of an either liquid or gaseous fuel with a comburent in particular constituted by a portion of the air heated by indirect heat exchange with the hot dichloroethane cracking products outflowing from said oven, if said air has been used as the high-temperature gaseous fluid for indirect heat exchange.

A second object of the present invention is an equipment system suitable to carry out the above disclosed process.

SUMMARY OF THE INVENTION

The system being the object the present invention comprises an oven with a radiant section and a convective section, equipped with heaters for either liquid or gaseous fuels, preferably installed in correspondence of the radiant section, the oven being provided in its interior with a first set of tubes in its convective section and with a second set of tubes in its radiant section, the set of tubes in the convective section being connected to pipes for the feed of fresh dichloroethane, and respectively the discharge of dichloroethane heated at a temperature lower than its boiling point, and the set of tubes of the radiant section being connected to pipes for the charging of vapourized dichloroethane, and for the discharging of the dichloroethane cracking products (among which, monomer vinyl chloride), and is characterized in that the tubes for the discharge of heated dichloroethane from the convective section lead to a first heat exchange device for vapourizing the dichloroethane, and that the tubes for the discharge of the dichloroethane cracking products lead to a second heat exchange device, which supplies the heat of the cracking product to a fluid, said fluid supplying in its turn heat to said first heat exchange device through a duct which places in said first and said second heat exchange devices in communication with each other, said duct being equipped with a burner for the initial heating of the fluid (in the absence of the cracking products) and for the possible decoking, and with a fluid circulator, the duct being furthermore provided with a pipe for the possible discharging of the fluid, and connected to a pipe for the delivery of the fluid, if air, as the comburent to the burners of the radiant section of the oven.

In a variant of the system of the present invention, the pipes supplying the heated dichloroethane to the first heat exchange device lead first to a separator, by which the dichloroethane vapour is separated from the liquid dichloroethane, which is continuously recycled by a pump through the said first heat exchange equipment and through said separator, the separator allowing also the possibly coked products to be separated.

The invention is now described with reference to the attached drawings, which are not to be intended as being limitative of the same invention.

DETAILED DESCRIPTION OF THE PREFERRED EMBODIMENTS

Figure 1:
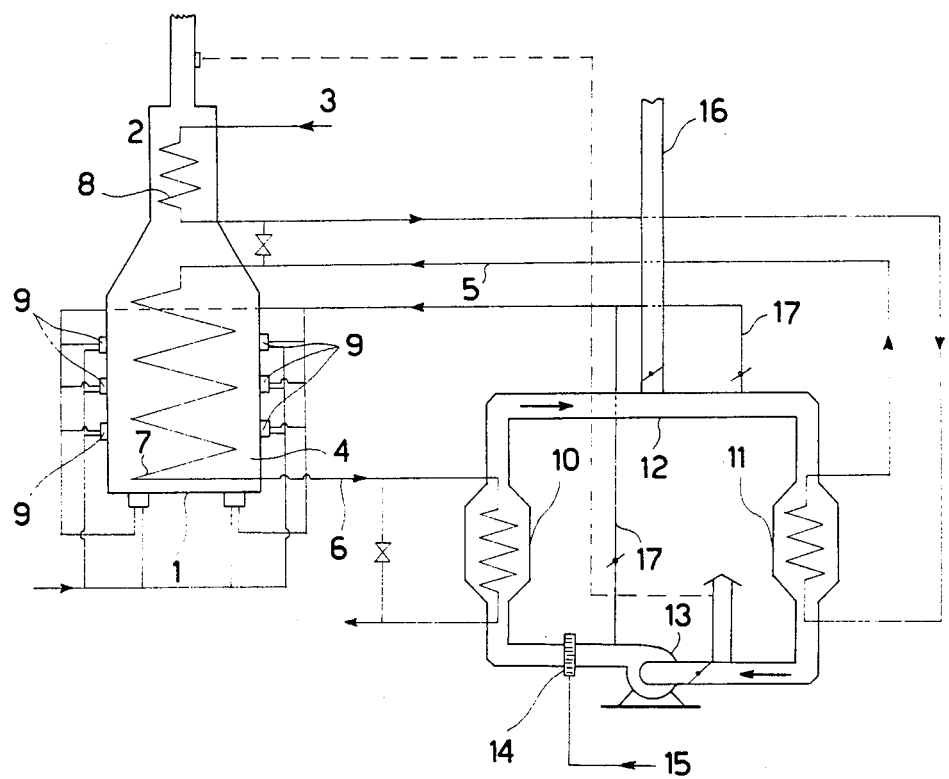
FIG. 1 is a schematic view of one embodiment of the apparatus of the invention.

Referring to FIG. 1 the oven (1) is composed by a convective section (2) wherein the liquid charge (3) of dichloroethane is preheated; this stream is preheated up to a temperature lower than its boiling point under the pressure corresponding to the outlet from the convective section, and hence remains in the liquid phase. The preheating takes place by means of the sensible heat of the products of combustion, which is carried out in the radiant section (4) of the oven to supply the heat for the overheating and the reaction of cracking of dichloroethane (5), which is recycled to the radiant section in the vapour phase. The products of reaction (6) leave the radiant zone at a temperature generally comprises with in the range of from 450° to 550° C. The preheating, the overheating and the reaction occur by heat transfer through tubes (7) and (8) suitably positioned in the radiant section and in the convective section. The burners (9) can be installed either on the side walls, or on the crown and/or in the bedplate of the oven.

The sensible heat of the products of reaction (6) is drawn in the refrigerator (10) and is transferred to the evaporator (11), wherein the vapourization of the charge previously preheated in the convective section (2) (8) of the oven is made take place. The fluid used to transfer heat from (10) to (11) is air, drawn from the atmosphere, or nitrogen, drawn from the plant system and circulated in system (12) by the fan (13).

Figure 2:
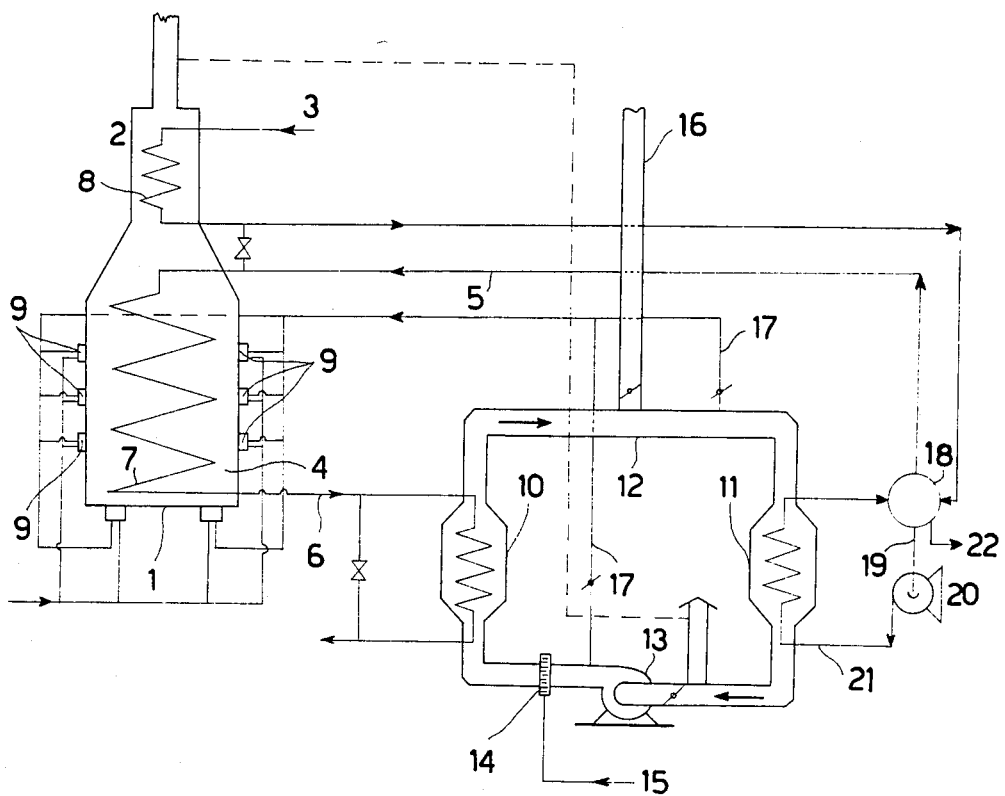
FIG. 2, is a schematic view of another embodiment of the apparatus of the invention showing recycling of the dichloroethane stream through a separator means.

By the dotted line in FIGS. 1 and 2 indicated has been the possible feed of the combustion products of the oven to the system (12).

Figure 3:
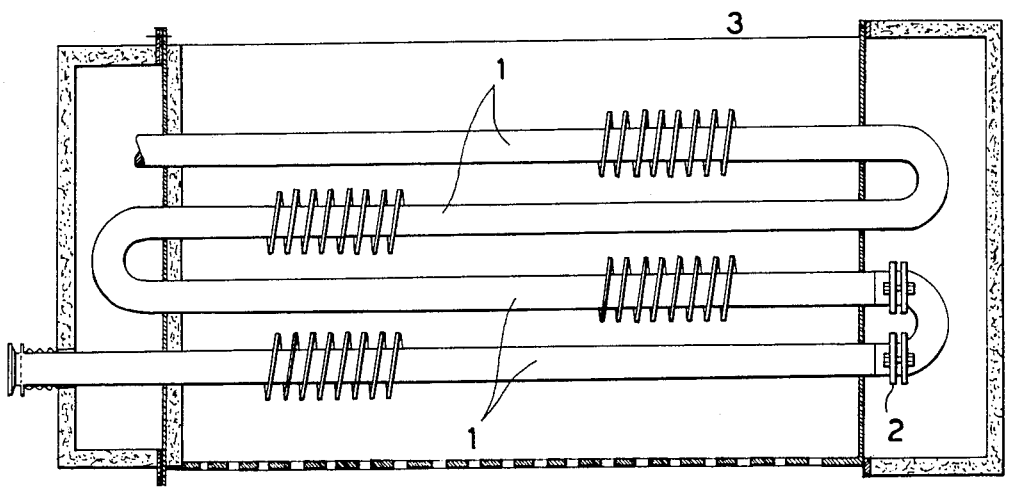
FIG. 3 is a schematic view of the heat exchangers employed in the apparatus of FIGS. 1 and 2.

The exchangers (10) and (11) are similar in structure to each other, and are constituted by the following components, as illustrated at FIG. 3:

Tube bundle constituted by finned tubes (1) with either cut or continuous fins having a height of up to 50 mm, a thickness comprised within the range of from 0.4 to 1.2 mm, and a density of up to 450 fins per meter, preferably of from 240 to 320 fins per meter; the tubes with nominal diameter of up to 10 inches are preferably connected to each other so to maintain the same number of passages on process side as inside the oven; the connection bends can be welded to the tubes, or they can be connected to the tubes by a flanged connection, which allows the access to the interior of the tubes, to carry out the mechanical cleaning, as indicated in FIG. 3, find number (2).

Figure 3A:
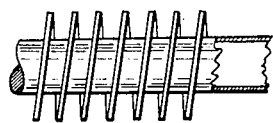
FIG. 3A is a cross-sectional view of a section of pipe employed in the heat exchangers shown in FIG. 3.
Figure 3A:
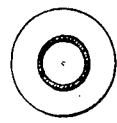
Figure 3A:
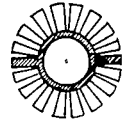

In FIG. 3A, details of types of fins are shown.

The tube-containing outer housing is tightly sealed relatively to the inner and to the outer pressure, and can be internally insulated by insulating and refractory materials, or it can be externally insulated by insulating materials. The inner coating is provided for the case in which the cleaning of the inner surfaces of the tube nest is carried out by the operation of decoking by air and steam, in which case the temperature of air surrounding the tube nest is increased up to the values typical for the execution of decoking operation, by means of the burner (14) installed in the fan (13) delivery duct.

The burner (14) is preferably of the multiflame gas burner type tubed inside the delivery duct (15) of fan (13), and supplies the heat for the decoking operation and for contributing to the starting up of the system.

The exchangers (10) and (11) are provided with a perforated distribution plate, air side, for the uniform distribution of the same air throughout the passage area.

The circulating air, which is heated in the exchanger (10) up to typical values of 200°-500° (C., releases its heat in exchanger (11) wherein, on tubes side, the vapourization of the dichloroethane charge occurs under less severe temperature conditions than it would find in the convective section of oven (2) and with higher exchange coefficient.

This exchanger allows hence a reduction to be achieved in fouling due to the breakdown and production of precursors of coke formation and allows consequently a longer operating time to be obtained between two subsequent cleaning operations.

The air circulation duct (12) is provided with a bypass stack (16) to be used during the decoking operations, installed downstream (10) or (11), as required by the cleaning needs.

From the same air circulation duct (12), a line (17) is branched, which conveys the preheated combustion air to the oven burners (9), which can be either of natural draught or of forced draught type, and can hence be fed with air under a pressure ranging from atmospheric pressure to some hundred water millimeters, typically 150-250 mm $H_2O$ gauge pressure. The combustion air is typically at the temperature of 200°-500° C., relatively to the amount circulated, to obtain the closure of the heat balance of exchangers (10) and (11).

In FIG. 2 the stream of dichloroethane, heated in (2) in the tube (8), is fed to a separator (18), vapour being obtained which is recycled to the oven through (5), as well as liquid which, through the pipe (19) is fed to pump (20), is then circulated via (21) through the vapourizer (11) and from here is passed through the separator (18), from which the coking products (22) are discharged.

We claim:

1. Apparatus for the production of vinyl chloride monomer by the thermal cracking of dichloroethane comprising:
   (a) an oven comprising a convective heating space and a radiant heating space;
   (b) means for supplying liquid dichloroethane to the convective heating space wherein the liquid dichloroethane is heated to a temperature below its melting point;
   (c) a first indirect heat exchange means for receiving the heated liquid dichloroethane from the convective heating space and for converting the heated liquid dichloroethane to gaseous dichloroethane;
   (d) means connected to the first heat exchange means for conveying the gaseous dichloroethane to the radiant heating space wherein the gaseous dichloroethane is further heated and thermally cracked to produce vinyl chloride monomer;
   (e) a second indirect exchange means for receiving the heated vinyl chloride monomer from the radiant heating space for recovering the vinyl chloride monomer; and
   (f) means for supplying a heat transfer fluid from said first heat exchange means to said second heat exchange means to thereby transfer heat from the heated vinyl chloride monomer to the heat transfer fluid in said second heat exchange means for use as the heat transfer fluid in the first heat exchange means.

2. The apparatus of claim 1 wherein the heat transfer fluid supply means comprises pipe means providing a circulatory pathway for supplying the heat transfer fluid from the first heat exchange means to the second heat exchange means and back to the first heat exchange means including means for circulating the heat transfer fluid through the pathway and an inlet for supplying fresh preheated heat transfer fluid to the pathway prior to entry into the second heat exchange means.

3. The apparatus of claim 1 further comprising separator means for receiving the heated liquid dichloroethane from the convective heating space and separating the heated liquid dichloroethane into a liquid dichloroethane portion and a first gaseous dichloroethane portion, circulating means for circulating the liquid dichloroethane portion to said first heat exchange means to thereby vaporize the liquid dichloroethane portion into a second gaseous dichloroethane portion, means for transferring said second gaseous dichloroethane portion to said separator, and pipe means connecting said separator to said radiant heating space for conveying said gaseous dichloroethane portions to said radiant heating space.

4. The apparatus of claim 3 wherein the separator means further comprises means for separating and removing coke and coke products.

5. The apparatus of claim 2 wherein the heat transfer fluid is air and wherein the heat transfer fluid supply means further comprises means connected to the pipe means for supplying a portion of the heated air from the second heat exchange means to the radiant heating space of the oven.

6. The apparatus of claim 1 wherein each of the first and second heat exchange means comprises a tube bundle comprising at least one fined tube having on the outer surface thereof a plurality of discontinuous or continuous fins.

7. The apparatus of claim 6 wherein the number of fins is up to 450 fins per meter of said tube.

8. The apparatus of claim 7 wherein the number of fins is from 40 to 320 fins per meter of said tube.

9. The apparatus of claim 6 wherein the tube bundle has a plurality of fined tubes connected together by flange means thereby forming a continuous pathway.

10. The apparatus of claim 6 wherein the fins have a height of up to 50 mm, a thickness of from 0.4 to 1.2 mm and the tube has a nominal diameter of up to 10 inches.

* * * * *